United States Patent [19]

Asano et al.

[11] Patent Number: 5,531,185

[45] Date of Patent: Jul. 2, 1996

[54] MANUFACTURING APPARATUS FOR USE IN A MICRO-GRAVITY ENVIRONMENT

[75] Inventors: Koji Asano; Atsushi Shiraishi; Hidefumi Ueda, all of Kawasaki, Japan

[73] Assignee: Fujitsu Limited, Kawasaki, Japan

[21] Appl. No.: 317,652

[22] Filed: Sep. 30, 1994

[30] Foreign Application Priority Data

Dec. 28, 1993 [JP] Japan .................................. 5-336689

[51] Int. Cl.⁶ ...................................................... C30B 7/14
[52] U.S. Cl. ......................... 117/206; 117/207; 117/901; 117/927
[58] Field of Search .................................... 117/901, 927, 117/206, 207

[56] References Cited

U.S. PATENT DOCUMENTS

| 4,917,707 | 4/1990 | Claramonte et al. . |
| 4,919,900 | 4/1990 | Martin et al. . |
| 5,013,531 | 5/1991 | Snyder et al. . |
| 5,078,975 | 1/1992 | Rhodes et al. . |
| 5,266,284 | 11/1993 | Heilig et al. ............................ 117/901 |
| 5,362,325 | 11/1994 | Shiraishi et al. ........................ 117/901 |

FOREIGN PATENT DOCUMENTS

| 4-367599 | 12/1992 | Japan . |
| 9214869 | 9/1992 | WIPO .................................... 117/901 |

*Primary Examiner*—Robert Kunemund
*Attorney, Agent, or Firm*—Armstrong, Westerman, Hattori, McLeland & Naughton

[57] ABSTRACT

A manufacturing apparatus which thermal design is easy, and which is small in size and light in weight is provided which is operated by a person in a micro-gravity environment. The manufacturing apparatus has a manufacturing unit having an operation side on which an operation is performed directly by the hand of an operator who faces the front of the facility, and a housing section for supporting the manufacturing unit slidably along the operation side and in such a manner as to be pulled out from the front of the apparatus to the outside. The manufacturing unit is housed with the operation side being vertical, and slides substantially horizontally. Also, an observation facility is disposed between two manufacturing unit housed in a constant-temperature tank so that the two facing sides of the member are observed simultaneously.

9 Claims, 9 Drawing Sheets

MANUFACTURING APPARATUS FOR USE IN A MICRO-GRAVITY ENVIRONMENT

BACKGROUND OF THE INVENTION

The present invention relates to a manufacturing apparatus which is used in a micro-gravity environment and which is directly and manually operated by a person in the micro-gravity environment.

The manufacturing of materials in a micro-gravity environment, such as in space, contributes considerably to the development of novel materials because materials can be manufactured which are difficult to manufacture on the ground under the influence of gravity. For example, in the biological engineering field, including protein engineering for designing molecular structures to create novel proteins having still higher functions, the manufacturing of bio-polymer crystals used as a sample for analyzing the structure and function of molecules, for example, crystals of protein or nucleic acid, is indispensable. When these bio-polymer crystals are manufactured on the ground under the influence of gravity, it is difficult to manufacture large crystals of high quality. Thus, it is expected that bio-polymer crystals will be manufactured using the micro-gravity environment of space.

If, however, these manufacturing apparatuses are all automated, it is difficult to obtain reliable results, particularly in the case of test manufacturing in which there are many indefinite factors. Thus, it is preferable that a person judges the situation and performs the appropriate operation. However, an experiment which is performed in space and which is intervened by the operation by a person becomes costly, the chances therefor are limited, and the limitations on the ease of operation are stringent. Thus, a manufacturing apparatus used in a micro-gravity environment is expected to perform a complete operation and must be provided with excellent ease of operation. In this connection, there has been a great demand for a manufacturing apparatus which is capable of reliably manufacturing materials and which is used in a micro-gravity environment in which ease of operation is excellent under a micro-gravity.

In a conventional manufacturing apparatus used to manufacture materials in a manned micro-gravity environment, for example, inside a manned artificial satellite, devices which are manually operated by a person are disposed on a horizontal plate surface. Such facility will be explained by using a manufacturing apparatus for manufacturing bio-polymer crystals as an example.

In this specification, the "horizontal" direction refers to such a direction from side to side and back and forth of the operator during operation when an operator, who takes a posture for performing an operation, is assumed to be standing or sitting vertically. Also, the "vertical" direction refers to a direction perpendicular to all the above-described horizontal directions, and is also simply called "vertical" or "up and down" without defining a reference.

Bio-polymer crystals are manufactured by mixing a precipitant solution with a bio-polymer solution in order to make the bio-polymer solution be supersaturated and by causing the bio-polymer crystals to become crystallized.

As the bio-polymer solution, a solution having salt reagents such as phosphate or acetate added as a buffer to a solution of a bio-polymer material, for example, protein, is usually used. As a precipitant solution, neutral inorganic salts of a high ion-strength, such as ammonium sulfate, cesium chloride, or sodium chloride, or organic solvents, such as polyethylene glycol, acetone, or ethanol, are usually used.

Although bio-polymer crystals are manufactured by mixing between a bio-polymer solution and a precipitant solution as described above, the reproducibility of crystal growth is not good because the binding force of the bio-polymer crystals is weak. Such poor reproducibility becomes a serious obstacle in an experiment under micro-gravity where the limitations of cost and chance are stringent. Because of this, a crystal manufacturing apparatus has been developed which is capable of reliably manufacturing crystals and is used in a micro-gravity environment by conducting a great number of experiments simultaneously at the same composition of materials and at the same growth conditions, or by varying the composition of the material or growth conditions little by little.

An apparatus for conducting such a number of experiments is usually constructed as follows.

Figure 1:
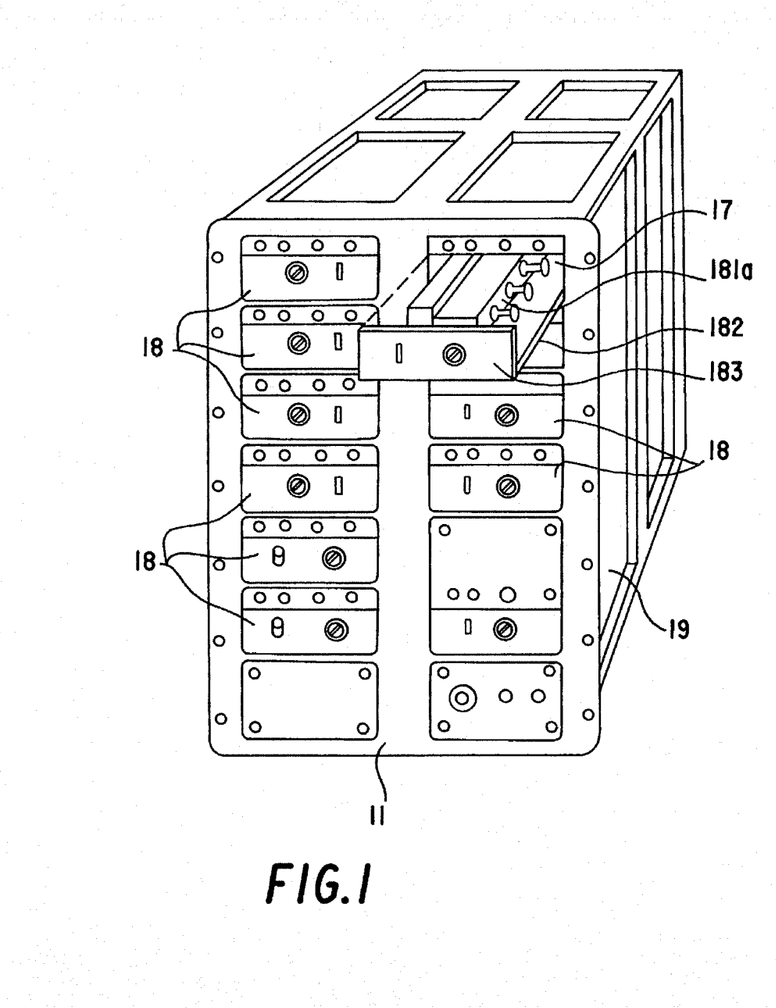
FIG. 1 is a general view of a conventional apparatus for manufacturing polymer crystals, which apparatus is used in a micro-gravity environment.

FIG. 1 is a general view of the prior art, and shows a conventional apparatus for manufacturing polymer crystals, which is used in a micro-gravity environment. Referring to FIG. 1, a block 181a has one or more cells which are provided with a portion where a manufacturing experiment is carried out, for example, a crystallization chamber where bio-polymer crystals are grown. The block 18(a) is replacably mounted on a plate-like cell mount 182. The whole of the cell mount 182 on which the block 181a is mounted constitutes a plate-like-shaped manufacturing unit 18 in the sense that the entire shape has the obverse and reverse surfaces. This manufacturing unit 18 is horizontally inserted into a housing section 17 from the front of the crystal manufacturing apparatus in such a way that a drawer is housed. A front plate 183, which is perpendicular to the cell mount 182, is usually securely disposed in the forward (the portion near the front of the apparatus during housing) tip of the cell mount 182. The front plate 183 covers the opening of the housing section 17 on the front panel of the apparatus. That is, the manufacturing unit 18 ordinarily constitutes a drawer-like construction having the cell mount 182 as the bottom plate. Further, a plurality of housing sections 17 are often disposed in the crystal manufacturing apparatus, and a great number of cell mounts 182 are mounted in the housing sections 17.

The cell mount 182 inserted into the facility is held inside a constant-temperature tank 19 or a thermostat which is surrounded by a thermal insulation material so that the cell mount 182, in a set of one or more, is maintained at a predetermined temperature at which crystals must be grown and stored.

A manufacturing apparatus having such construction has a great number of portions where a manufacturing experiment is carried out, for example, crystallization chambers, and further, the portion where a manufacturing experiment is carried out can be replaced with a new one by replacing the block 181a. Accordingly, it is possible to conduct a great number of manufacturing experiments easily by using one crystal manufacturing apparatus.

However, in the conventional manufacturing apparatus, as in a bio-polymer crystallization apparatus of FIG. 1, the cell mount 182 is horizontally mounted in the housing section 17 disposed in the front panel 11 of the apparatus. However, in the conventional construction in which the manufacturing unit 18 having an operation mechanism, such as the cell mount 182, is horizontally mounted, the surface side on which the device, in which a manufacturing experiment is carried out, is mounted becomes an operation side where the operation is performed. Hence, the following problem occurs.

When a person works in a room in a micro-gravity environment, such as in a manned artificial satellite, it is common that his legs and one of his hands are fixed, and the operation is performed by the remaining free hand. To secure the fixed positions of his hands and feet, the vertical direction is set in the room. Because of this, the apparatus employed in a micro-gravity environment is manufactured and used by defining the vertical direction thereof, so that the apparatus has it's top and bottom. That is, such apparatus is designed so that the operator operates the facility with one hand while looking at the apparatus from in front and above the apparatus.

Since in the conventional apparatus having the manufacturing unit 18 mounted horizontally thereon it is impossible to view the rear surface of the manufacturing unit 18 from above, it is difficult to operate an apparatus disposed on the rear surface of the manufacturing unit 18. For this reason, all apparatuses to be operated, for example, the blocks 181a, are preferably disposed on the top surface of the manufacturing unit 18.

However, the housing section 17 is usually disposed inside the constant-temperature tank 19. Because of this, if the apparatuses to be operated are disposed on the top surface of the manufacturing unit 18, for example, on only the top surface of the cell mount 182, the symmetry of the manufacturing unit 18 deteriorates, and the thermal design of the constant-temperature tank 19 for housing the manufacturing unit 18 becomes difficult.

It is desired, in addition to the above-described construction, that means for observing the process or result of the experiment, for example, the process or result of the crystallization be disposed to increase the efficiency of the experiment. Such observing means is accomplished, for example, by using a block made of a transparent material and by observing it using a CCD camera from outside the constant-temperature tank through a window provided therein. However, the window provided in the constant-temperature tank is inferior in thermal insulation characteristic. Accordingly, it is difficult to make the temperature distribution inside the constant-temperature tank uniform.

Another problem which occurs when the manufacturing unit is mounted horizontally is that it is difficult to reduce the number of observation facilities, which are observing means, and to reduce the volume and weight of the apparatus. That is, in the conventional apparatus in which the above-mentioned manufacturing unit is mounted horizontally, the devices to be operated and the devices to be observed are disposed on the top surface of a manufacturing unit which can be checked visually and which is easy to operate. For this reason, one observation facility must be disposed for each cell mount. Because of this, the number of observation facilities is not reduced, and therefore the volume and weight of the apparatus is not reduced.

Figure 2:
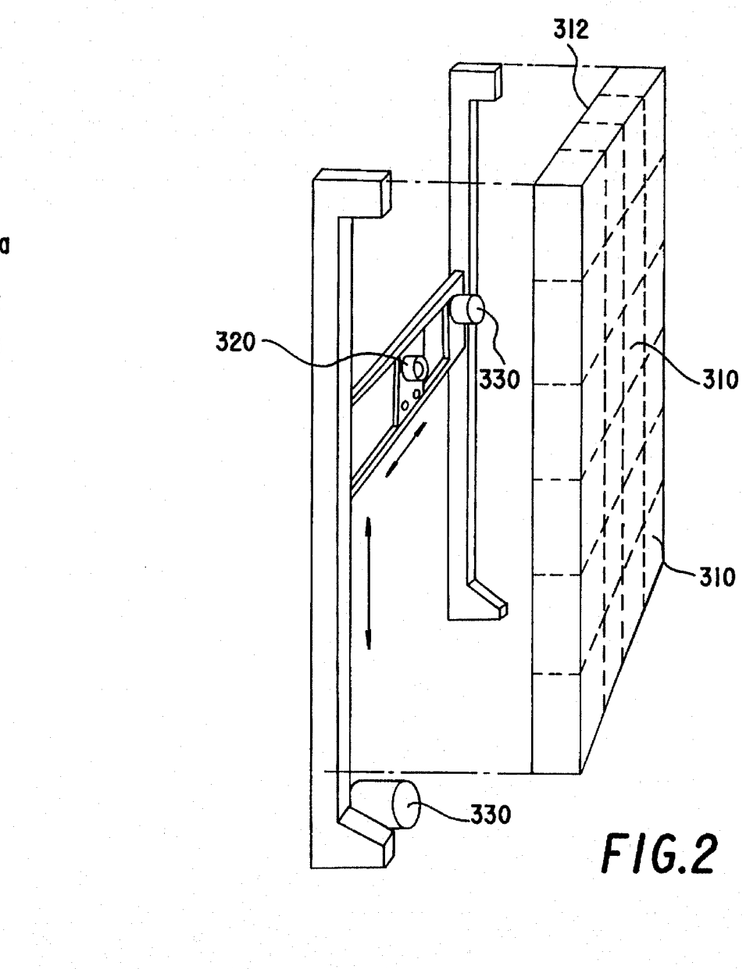
FIG. 2 is a perspective view of a conventional observing apparatus, and also shows the observing means of the apparatus disclosed in the prior art.
Figure 3:
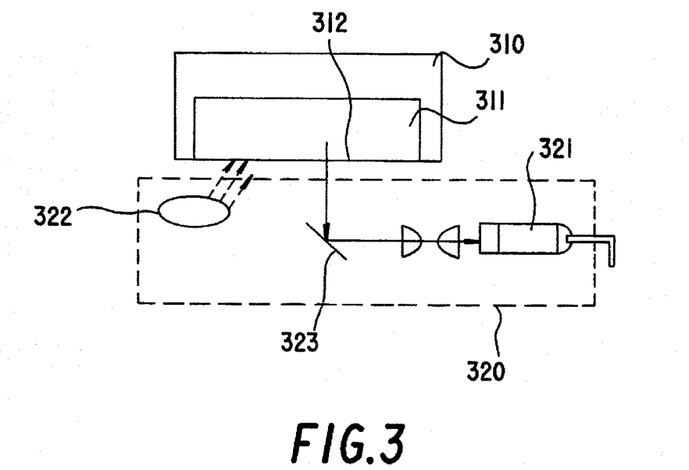
FIG. 3 is a conceptual view of the conventional observing unit, and also is a sectional view illustrating the operation of the observing unit in FIG. 2.

To solve such problem, a bio-polymer crystal manufacturing apparatus having one observation facility for observing a plurality of the device to be observed which are disposed on one surface of the above-mentioned manufacturing unit, for example, a great number of cell mounts, has been invented and is disclosed in Japanese Patent Laid-Open No. 4-367599. Referring to FIGS. 2 and 3, in this apparatus, blocks 310 having an observation window 312 for observing in a crystallization chamber 311 housed in the block 310, the temperature of which is controlled individually, are arrayed in such a way that the observation windows 312 are aligned in the form of a two-dimensional lattice. The observation facility has an observing unit 320 having a CCD camera 321 mounted thereon which is driven by a scanning motor 330 and scanned two-dimensionally, and observes the crystallization chamber 311 from the observation windows 312 which are arrayed two-dimensionally. A mirror 323 is used to observe the observation window 312 in a direction at right angles to the optical axis of the CCD camera 321. An illumination unit 322 is moved vertically together with the CCD camera 321 and illuminates the crystallization chamber 311 through the observation window 312.

In this apparatus, to maintain respective blocks 310 each at a different temperature, each block 310 is thermally insulated, and thus each block forms one constant-temperature tank. However, since in this construction the observation window 312 causing an inferior heat insulation effect is required in one of the blocks 310, it is difficult to make the temperature distribution in the block 310 uniform. Furthermore, to make the COD camera 321 perform two-dimensional scanning, two long arms which intersect crosswise and scan vertically and horizontally by the scanning motors 330, respectively, are required. For this reason, it is difficult to form the facility of a strong construction which can withstand the vibrations which occur during a launching of the apparatus into a space environment or during a return to the ground from a space environment.

SUMMARY OF THE INVENTION

According to the present invention, a manufacturing apparatus used in a micro-gravity environment is provided, the apparatus having a top and a bottom, and having a front panel disposed at a position intermediate between the top and the bottom, comprising, a manufacturing unit comprising a plate or frame-like member having a plane on which at least one of devices operated by at least one hand of an operator is arranged, the operator facing the front panel and directing his head to the top, a housing section for housing therein the manufacturing unit, and slidably supporting the manufacturing unit so that the plane of the plate or frame-like member of the manufacturing unit is in parallel to an axis directing form the bottom to the top and the manufacturing unit is drawn out from the apparatus through an opening provided in the front panel. A pair of the manufacturing units may be housed in the housing section so that the respective planes of the plate or frame-like members are in parallel to each other, and the respective devices on the plate or frame-like members are arranged mirror-symmetrically each other. Furthermore, an observation facility for observing the respective devices on the plate or frame-like members of the pair of manufacturing units, may be disposed between the respective plate of frame-like members of the pair of manufacturing units. The observation facility may comprise a detector and a mechanism for moving the detector to scan the respective planes of the plate or frame-like members in order to observe the plural devices.

When thermal insulation means enclosing the housing section at a constant-temperature is disposed, the thermal insulation means has a portion corresponding to the opening provided in the front panel, which portion is made separable from the apparatus in order to draw out the manufacturing unit from the apparatus. Each of the devices may comprise a crystallization cell block for growing therein bio-polymer crystals, the crystallization cell block being provided with a window for observing the crystals growing therein.

It is an object of the present invention to provide a manufacturing apparatus for use in a micro-gravity environment, in which apparatus the device operated by a hand is in a vertical plane of the plate or frame-like member so that the apparatus is suited to be operated with one hand while checking the operated device visually.

It is another object of the present invention to provide a manufacturing apparatus in which the symmetry of the manufacturing unit and the inside of the constant-temperature tank is improved, and thermal design is easy, and which is used in a micro-gravity environment.

It is a further object of the present invention to provide a manufacturing apparatus used in a micro-gravity environment, which apparatus is easy to operate, and small in size and light in weight.

It is a still further object of the present invention to provide a manufacturing apparatus used in a micro-gravity environment, which apparatus is easy to operate, is small in size and light in weight, and has high resistance to vibrations.

The above and further objects, aspects and novel features of the invention will more fully appear from the following detailed description when the same is read in connection with the accompanying drawings.

DETAILED DESCRIPTION OF THE PREFERRED EMBODIMENTS

First, a brief description of the present invention will be given with reference to the embodiments.

Figure 4:
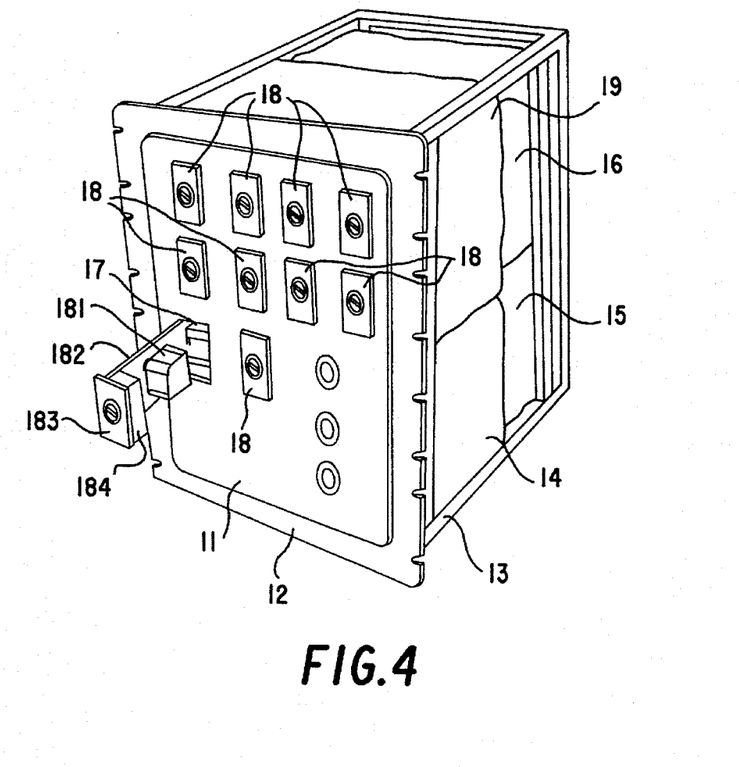
FIG. 4 is a general view of a first embodiment of the present invention, and illustrates a manufacturing apparatus for manufacturing bio-polymer crystals.
Figure 5:
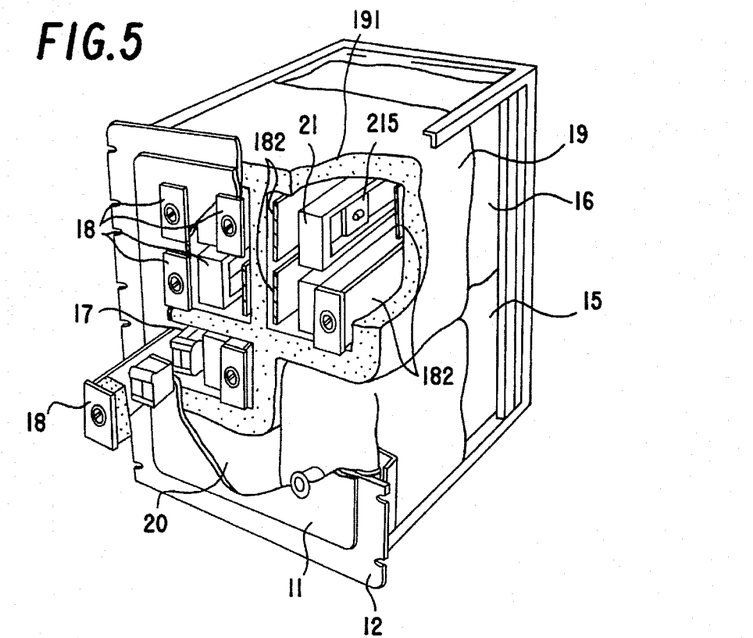
FIG. 5 is a partially cutaway view of FIG. 4, and illustrates a manufacturing apparatus for manufacturing bio-polymer crystals.

In the present invention, referring to FIGS. 4 and 5, a manufacturing unit 18 with a plate-like member, for example a cell mount 182, is drawn out to the front of an operator from the front panel of the apparatus, so that the plane of member is kept vertically. Thus, the operator can operate on both sides of the plate-like member the manufacturing unit 18 by merely moving his head portion from side to side without greatly moving the whole body and by using his right and left hand alternately while looking at the operation side on which the operated device disposed.

Thus, unlike in the conventional facility, there is no need to operate on the bottom surface of the manufacturing unit, and therefore the operation becomes easier. Further, in this construction, even if both sides of the manufacturing unit are used as operation sides, ease of operation is not deteriorated. Since both sides of the member can be designed to be symmetric so as to increase the symmetry of the manufacturing unit, thermal design is easy. Also, since the symmetry of the interior of the constant-temperature tank 19 for housing the manufacturing unit 18 increases, the thermal design of the constant-temperature tank 19 becomes easy.

Further, the operation sides of the two manufacturing unit 18 having an operation side on only one side are made to face each other, or the opposite sides of the operation sides are made to face each other, and are housed so as for the operation side become vertical. Since the two facing manufacturing unit 18 usually show a shape close to a mirror symmetry, the symmetry as the whole of the two manufacturing unit 18 is higher than that of a single manufacturing unit 18. On account of this, thermal design of the constant-temperature tank 19 becomes easy. When a person performs an operation in this construction, one of the two manufacturing unit 18 in a pair is pulled out, and is operated by, for example, the right hand. In a similar manner, it is possible to pull out the other facing manufacturing unit 18 and operate it with the left hand. As a result, the ease of operation can be maintained.

Figure 7:
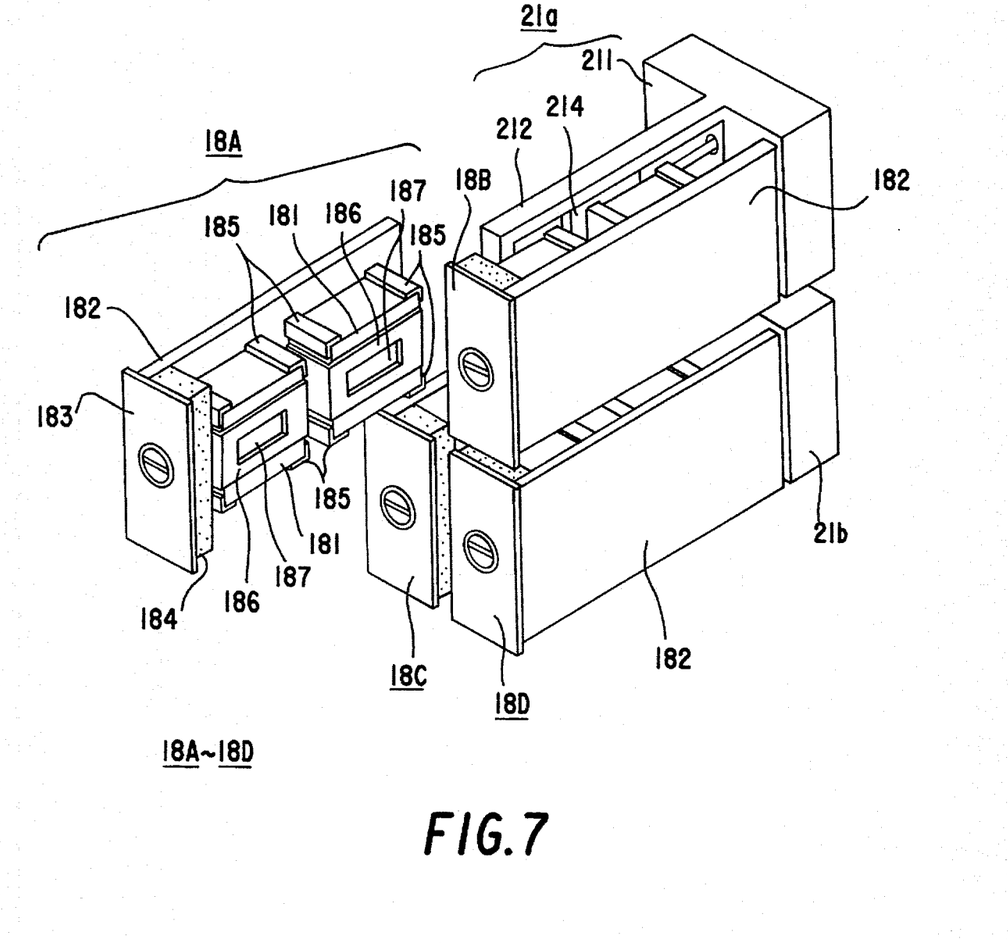
FIG. 7 is a view illustrating the construction of the interior of the drawer housing section, and also illustrating the positional relationship between a cell mount housed in the housing section and an observation facility in accordance with the first embodiment of the present invention.

Furthermore, a observation facility for observing crystal growing may be disposed in the apparatus for manufacturing bio-polymer crystals. Referring to FIGS. 5 and 7, two manufacturing unit 18A and 18B, in a pair, are housed inside one housing section 17 together with one observation facility 21*a*. These manufacturing units 18A and 18B have on one side an observation window 187, disposed in the block 181, for observing an object to be observed, for example, a crystallization chamber. The pair of manufacturing units 18A and 18B are housed in the housing section 17 in such a way that a space by which the observation facility 21*a* can be disposed is provided in a condition in which the side on which these objects to be observed are mounted are made to face each other, and the operation side of the member 18 becomes vertical. The observation facility 21*a*, disposed between a pair of manufacturing unit 18A and 18B which face each other, observes the surface of the manufacturing units 18A and 18B on both sides of the observation section 21*a*, for example, the observation window 187 of the block 181 disposed on the cell mount 182.

In the above apparatus, it is possible to observe the facing surfaces of the pair of manufacturing units 18A and 18B using one observation facility 21*a*. Thus, the volume and the weight of the apparatus can be reduced. Also, since the manufacturing units 18A and 18B are always housed in the housing section 17 as a pair, the symmetry of the entire assembly housed in the housing section 17 is high because of the same reason described above, and thermal design is easy. Further, since the observation facility 21*a* is also housed in the same housing section 17 together with the manufacturing units 18A and 18B, it is unnecessary to provide an observation window in the constant-temperature tank 19 and it becomes possible to make the temperature distribution in the constant-temperature tank 19 more uniform. The front plate 183 for covering the opening of the constant-temperature tank 19 improves thermal insulation of the wall of the constant-temperature tank 19 so that the temperature is made uniform and ease of control is improved. Each constant-temperature tank 19 may be divided into a plurality of thermally insulated chambers, each of which houses each housing section 17 therein and thermal insulation of each thermally insulated chamber on the front panel of the apparatus is performed by a thermal insulation plate 184 disposed on the rear surface of the front plate 183. Since in such construction the thermal insulation efficiency of the whole thermally insulated chamber is high and thermal interference between the thermally insulated chambers is small, it is possible to perform precise temperature control. Since in the above-described embodiment the manufacturing units 18A and 18B are pulled out with the operation side being vertical, it is possible to easily operate the operation mechanism disposed in the cell mount 182. Further, the provision of the operation side and an object to be observed on only one side of the member improves the ease of operation even more.

Figure 11:
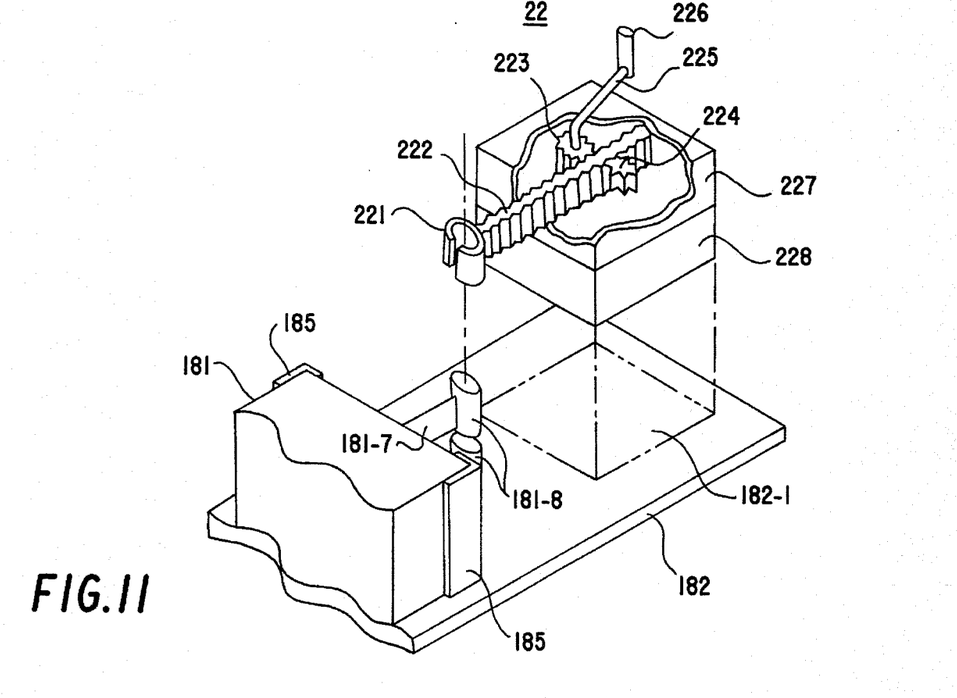
FIG. 11 is a partially cutaway view illustrating the construction and the mounting position of a jack in accordance with a second embodiment of the present invention.
Figure 12A:
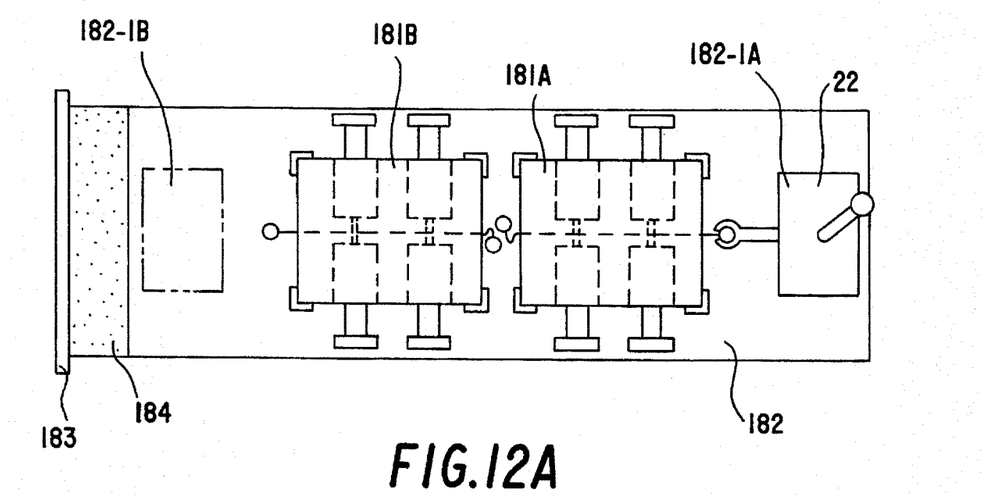
FIG. 12A is a plan view of a cell mount in accordance with a second embodiment of the present invention, also illustrating the relationship between the jack mounting position and the block position on the cell mount.
Figure 12B:
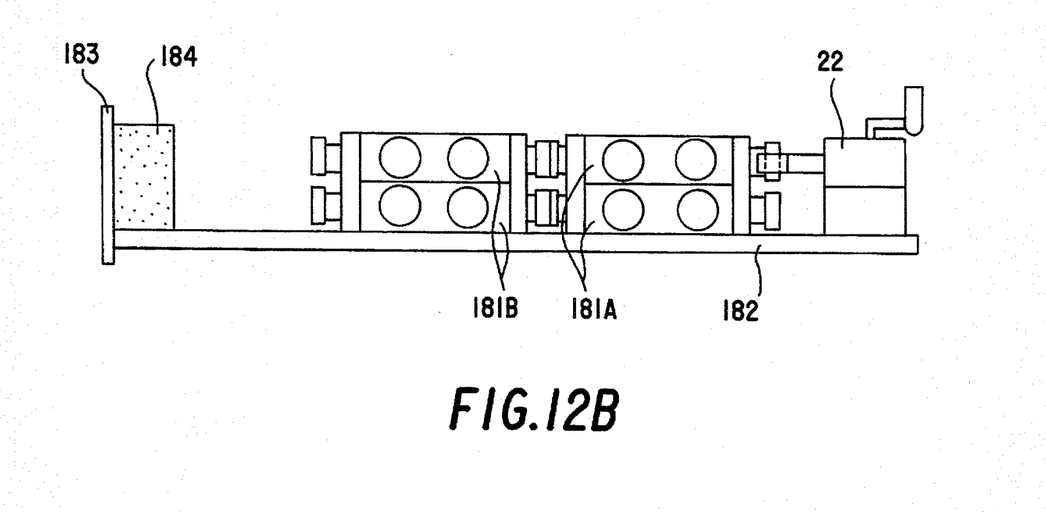
FIG. 12B is a front view of a cell mount in accordance with a second embodiment of the present invention, also illustrating the operation of the block using the jack.
Figure 13:
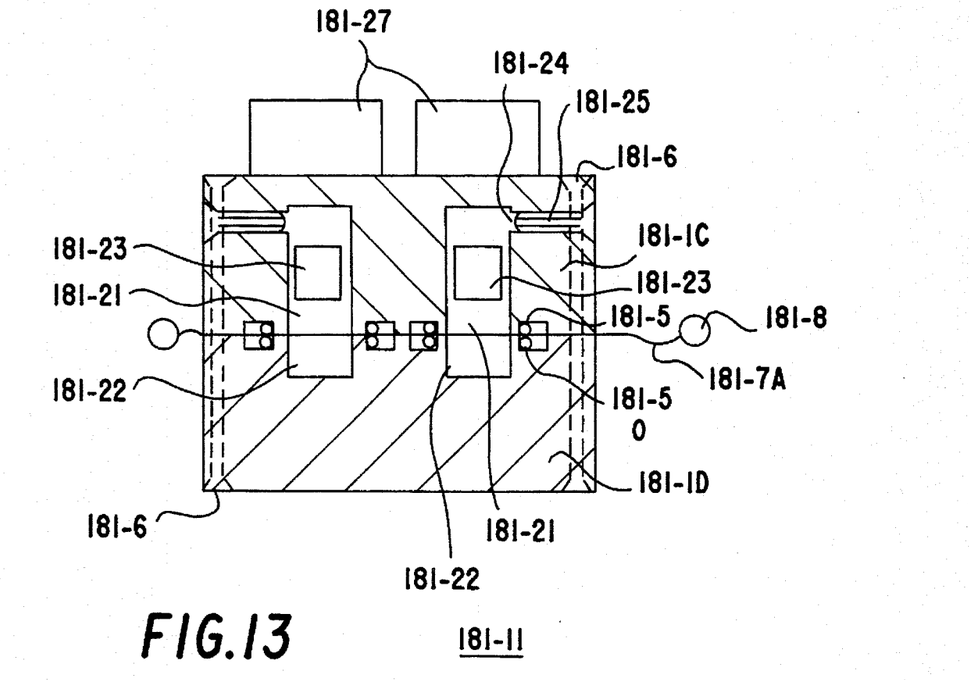
FIG. 13 is a vertical (parallel to the surface of the cell mount) sectional view illustrating the construction of a block in accordance with a third embodiment of the present invention.

Referring to FIGS. 7 to 9 related to a first embodiment of the present invention and FIGS. 13 and 14 related to a third embodiment of the present invention, operations performed on the operation side include replacement of the block 181, injection of materials to a crystallization chamber 181-11 (see FIG. 8), the operation of the block 181 such as opening/closing of slit valves 181-7 (see FIG. 9) and 181-7A (see FIG. 13). Referring to FIGS. 11, 12A and 12B related to a second embodiment of the present invention, operations performed on the operation side include mounting of an apparatus for making the operation of the block 181 easy and the operation of the apparatus, and fixation of the pulled-out manufacturing unit 18. There are strong demands in many of these operations that the operation be operated while looking at an object to be observed, for example, a block, in order to confirm the state of the crystallization chamber and the storage of the material, and the normal operation of the block. In such a case, if an operation portion is provided on the side on which an object to be observed is present, it is possible to operate the object with one hand while looking at it from one side. Thus, excellent ease of operation is realized.

Figure 10:
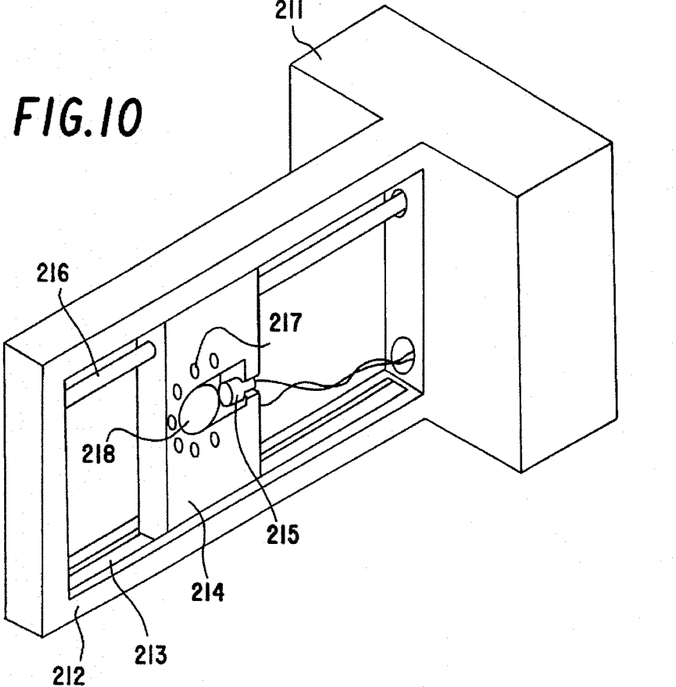
FIG. 10 is a perspective view illustrating the construction of an observation section in accordance with the first embodiment of the present invention.

With reference to FIG. 10, the above-described observation facility can be designed to scan a detector in only one direction. As a result, the scanning mechanism is simplified to increase reliability, and the construction can be simplified to achieve high resistance to vibrations. Further, the observation facility becomes small in volume and light in weight. It is also possible to form the observation facility into a construction by which both sides are observed simultaneously. As a result, since a mechanism for switching the optical path in the optical system can be omitted to simplify the mechanism, it is possible to make the observation facility have high resistance to vibrations and be small in size.

The present invention will be explained below with reference to the preferred embodiments.

A first embodiment of the present invention is concerned with a apparatus for manufacturing bio-polymer crystals, which apparatus employs a batch method.

Figure 9A:
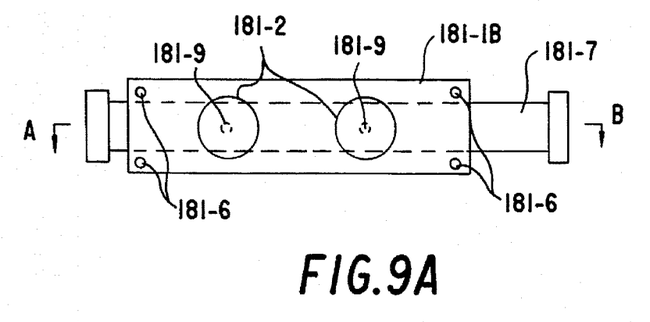
FIG. 9A is a front view of the block, illustrating a block used in a batch method in accordance with the first embodiment of the present invention.
Figure 9B:
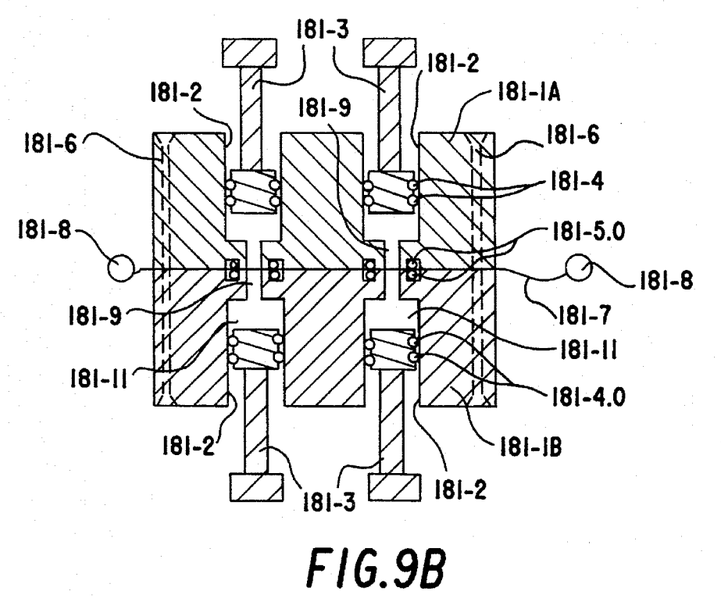
FIG. 9B is a horizontal sectional view of a block in accordance with the first embodiment of the present invention, which is taken along the line A–B of FIG. 9A.

A cell of the batch method will be explained first. Referring to FIGS. 9A and 9B, two resin blocks 181-1A and 181-1B, made of transparent material, for example, epoxy, are made to abut at the end surface, they are secured by a set of screws 181-6 and formed into one unit, forming a block of a rectangular parallelepiped. In the resin blocks 181-1A and 181-1B, a syringe 181-2 is punched from the end surface on a side opposite to the abutting end surface, and a pore 181-9 for connecting the syringes 1812 provided in the two resin blocks 181-1A and 181-1B is provided from the tip of the syringe 181-2.

A piston 181-3 which slides inside the syringe 181-2 is disposed and an O-ring 181-4 is provided on the outer periphery of the piston 181-3.

Figure 9C:
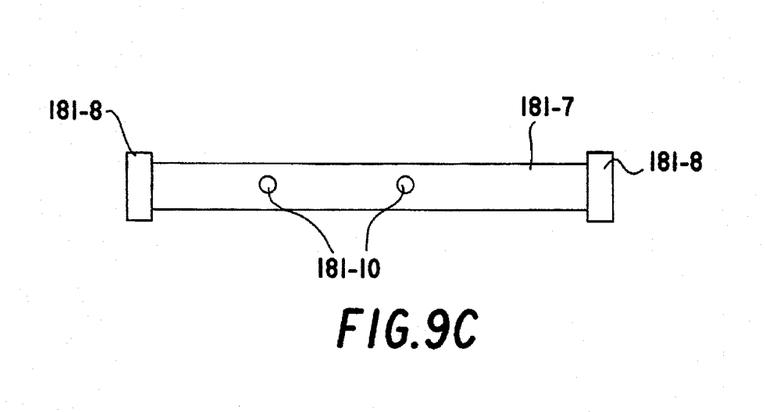
FIG. 9C is a front view of a slit valve in accordance with the first embodiment of the present invention, illustrating the construction of the slit valve of FIG. 9A.

A slit valve 181-7 for opening/closing the pore 181-9 is disposed on the surface at which the two resin blocks 181-1A and 181-1B which form the block are abutted. The slit valve 181-7 shown in FIG. 9C is formed of a thin metallic sheet having Teflon or the like coated thereon, and as many as the number of slit-holes 181-10 at a position corresponding to the pore 181-9, for example, two slit-holes 181-10, are provided for two pores 181-9. Thus, by making the slit valve 181-7 slide along AB of FIG. 9A, a plurality of pores 181-9 can be opened (or closed), simultaneously. A cylindrical bar-shaped stopper 181-8 is fixed at both ends of the slit valve 181-7. The stopper 181-8 serves as a grip portion for pulling out the slit valve 181-7 and is used as a stopper for securing the position of the slit valve 181-7. An O-ring 181-5 surrounding the pore 181-9 is provided on the sliding surface of the slit valve 181-7 so that the contents of the bio-polymer solution or the precipitant solution are prevented from leaking from the pore 181-9.

In the batch method, a precipitant solution is prestored in the syringe 181-2 disposed in one of the resin blocks, 181-1A, before a crystal is grown, and a bio-polymer solution is prestored in the syringe 181-2 provided in the other resin block 181-1B. Before the crystal-growth starts, these two solutions are separated by the slit valve 181-7.

To make the crystal-growth start, initially, the slit valve 181-7 is made to slide, the pore 181-9, which connects two syringes 181-2, is made to coincide with the slit-holes 181-10. Then, the piston 181-3 inside the syringe 181-2 where the precipitant solution is stored, and the piston 181-3 inside the syringe 181-2 where the bio-polymer solution is stored are alternately pushed in for several times so that the precipitant solution and the bio-polymer solution are mixed. After mixing, the mixed solution is collected in one of the syringes selected as the crystallization chamber 181-11, for example, the syringe 181-2 in which the bio-polymer solution has been stored. Thereafter, to prevent the piston 181-3 from moving hereinafter, the slit valve 181-7 is made to slide to its original position to close the pore 181-9. As a result of the mixed solution being left at rest, the crystal is grown in the syringe 181-2 where the biopolymer solution has been stored, which syringe 181-2 is made as the crystallization chamber 181-11.

Next, the cell mount will be explained. In this embodiment, the above-described block is mounted on the cell mount which forms a drawer construction.

Figure 8A:
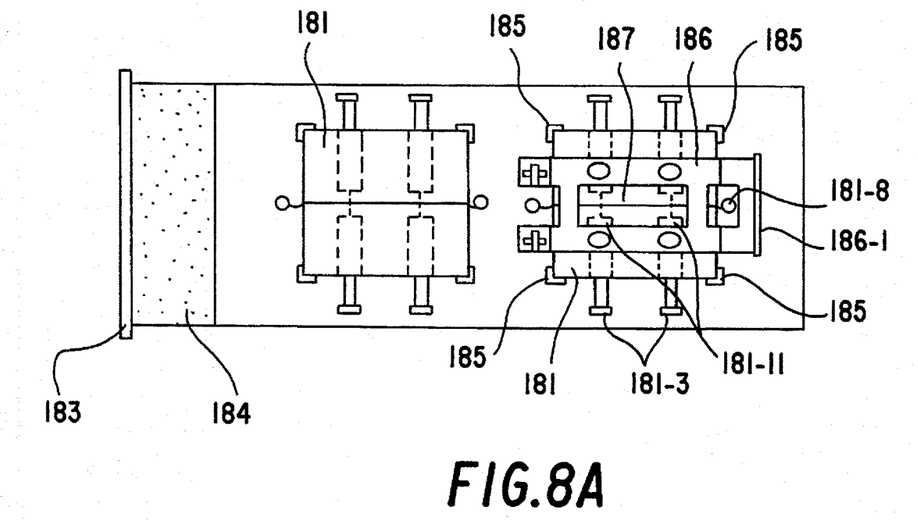
FIGS. 8A and 8B are views of a cell mount, illustrating a mechanism for mounting a block on the cell mount in accordance with the first embodiment of the present invention.
Figure 8B:
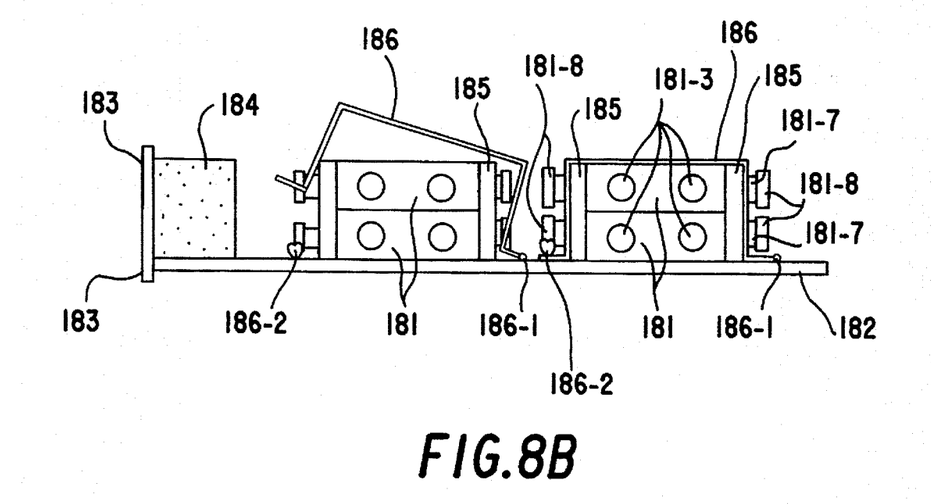

Referring to FIG. 8B, the cell mount 182 formed of a plastic plate is fixed to the lower end of the front plate 183 perpendicularly and in the shape of a letter L, thus forming the bottom plate portion of a drawer-like manufacturing unit 18A (see FIG. 7) which is formed together with the front plate 183. In the L-shaped corner at which the front plate 183 and the cell mount 182 are fixed, a thermal insulation material 184 is attached on the cell mount 182 so as to be in contact with the front plate 183 and to cover the rear surface of the front plate 183. Referring to FIG. 5, when the manufacturing unit 18 is inserted into the housing section 17, the thermal insulation material 184 becomes a part of a thermal insulation material 191 which forms the thermal insulation wall of the constant-temperature tank 19.

With reference to FIG. 8, a fastener 185 and a presser 186 are disposed on the cell mount 182 in order to mount the block 181 thereon. Fasteners 185 are members for determining the position at which the block 181 is mounted, and are column-like members the cross section of which is in the shape of a letter L, in a set of four, which are implanted at positions corresponding to the four corners of the block 181. The block 181 is loosely inserted between four fasteners 185, and positioned in place in a rectangular region demarcated by these four fasteners 185. The fasteners 185 are made to have a height corresponding to that when the block 181 is mounted in a stacked manner, and are implanted at a plurality of places when the blocks 181 are mounted at a plurality of positions on the cell mount. In this embodiment, referring to FIG. 8, blocks 181 are stacked in two steps, and mounted in two places on the cell mount. The presser 186 is a member for pressing the block 181 which is loosely inserted between the fasteners 185, and is made of a metallic thin plate, the cross section of which is in a hat shape, which is in close contact with the top surface and both sides of the block 181. A jaw in the lower end of the presser 186 is brought into close contact with the surface of the cell mount 182, and the end of one of the jaws is hinged to the cell mount 182 by a rotatable rotary section 186-1, and the other jaw is mounted on the cell mount 182 by a wing screw 186-2.

The block 181 is replaced as follows: first, the wing screw 186-2 is removed, then one end of the presser 186 is lifted (see the block and the presser on the left of FIG. 8B) and the block 181 is removed from the fastener 185, then a new block is inserted into the fastener 185, and the presser 186 is made to cover the block 181 and fixed by the wing screw 186-2. The observation window 187 for observing the crystallization chamber 181-11 provided in the block 181 is provided on the top surface of the presser 186. A portion in abutment with the slit valve 181-7 and the stopper 181-8 is punched so that the portion do not come into contact with them.

Figure 6:
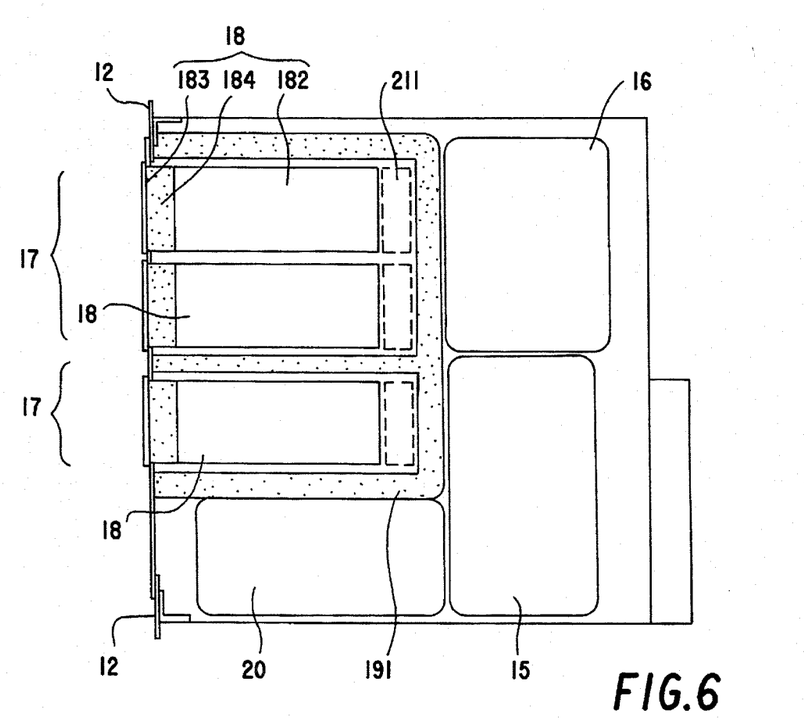
FIG. 6 is a longitudinal sectional view of the first embodiment of the present invention, and illustrates the mounting positions of the housing section and the constant-temperature tank in the entire facility.

Next, the mounting of the cell mount will be explained. Referring to FIGS. 4, 5 and 6, in a apparatus for manufacturing bio-polymer crystals in accordance with this embodiment, the constant-temperature tank 19 is incorporated into the upper portion on the front of a chest member formed of a bay load drawer frame 13 and a bay load drawer front panel 12 having a front panel 11 mounted thereon, an observing unit control section 14 and a power-supply section 20 are incorporated into the lower portion on the front of a chest member, a control section 16 is incorporated into the upper portion in the inner part of the chest member, and a heat exchange section 15 is incorporated into the lower portion in the inner part of the chest member.

The cell mount 182 is inserted into the housing section 17, serving as the bottom of the drawer-like manufacturing unit 18, which is opened on the front panel 11 and provided inside the constant-temperature tank 19. Referring to FIG. 5, the manufacturing unit 18 is mounted in one partition of the constant-temperature tank 19 surrounded by the thermal insulation material 191, in one or two sets of two manufacturing units 18 (two manufacturing units 18 in a set).

Next, a description will be given of an example in which two sets of two manufacturing units 18 are mounted in one partition of the constant-temperature tank 19. This one partition constitutes a thermally insulated chamber.

Referring to FIG. 7, four drawer-like manufacturing units 18A to 18D, and two observation sections 21a and 21b are housed in one partition of the constant-temperature tank in such a way that they are placed in two upper and lower steps. More specifically, with two manufacturing units 18A and 18B as a set, they are placed in the upper step together with one observation facility 21a, and with the remaining two manufacturing units 18C to 18D as another set, they are placed in the lower step together with one observation facility 21b.

The arrangement of the upper step will be explained first. Referring to FIG. 7, the observation facility 21a is secured in such a way that a guide frame 212 is present (see FIG. 10) in the vertical plane which separates the corresponding partition of the constant-temperature tank. Referring to FIG. 10, a guide groove 213 is provided in the inner portion of the upper and lower frames of the guide frame 212. A scanning block 214 having an optical system for observation purposes mounted thereon is moved in the back and forth direction of the apparatus (along the depth of the apparatus) along the guide frame 212. This movement is done by making a screw 216 screwed to the scanning block 214 be driven forward or backward by a motor housing 211 disposed in the inner part of the guide frame 212.

The optical system for observation purposes comprises a detector such as an image pick-up tube 215 employing a CCD (charge coupled device), and lenses 218 provided on the right and left of the scanning block 214, and lamps 217. The lenses 218 provided on the right and left both sides, together with two reflecting mirrors (not shown) provided so as to have an angle of 45° with respect to the optical axis of the lenses 218 and the image pick-up tube 215, respectively, bring objects to be observed on the right and left of the scanning block 214 to an image on one side of the CCD, respectively. The lamps 217 are provided to illuminate the objects to be observed.

Referring to FIG. 7, the set of the manufacturing units 18A and 18B in the upper step are disposed in the housing section 17 on both sides of the observation facility 21a in a condition in which the cell mount 182 is made vertical and the observation window 187 is made to face the observation facility 21a.

The arrangement in the lower step including the manufacturing units 18C to 18D and the observation section 21*b* is the same as the above-described arrangement in the upper step. Therefore, in this facility, crystals are grown simultaneously at the same temperature in 16 blocks 181 mounted stacked in two steps in each of the four manufacturing units 18A to 18D, that is, 32 crystallization chambers 181-11.

In the first embodiment, referring to FIG. 4 or FIG. 5, two housing sections 17 for housing four manufacturing units 18 in one partition of the constant-temperature tank 19 are disposed in the upper portion on the front of the apparatus, and further the housing section 17 for housing two manufacturing units 18 is disposed in one partition of the constant-temperature tank 19 below the former one. Thus, it is possible to grow crystals at three different temperatures simultaneously by using three partitions of the constant-temperature tank 19.

Next, a description will be given of the operation of the first embodiment of the present invention. First, referring to FIGS. 7 to 9, the body of the operator is fixed by one hand in an experiment chamber under a microgravity inside an artificial satellite, and one manufacturing unit 18A is pulled out by the other hand. Then, the wing screw 186-2 on the cell mount 182 is removed to open the presser 186. Next, the block 181 is inserted between the fasteners 185 on the cell mount 182 as described above, and the presser 186 is made to cover it and fixed by the wing screw 186-2.

Next, the manufacturing unit 18A is housed in the housing section 17, and the other manufacturing unit 18B, which is formed in pair with the manufacturing unit 18A, is similarly housed in the housing section 17 with the block 181 fixed. Such operation is repeatedly performed for all the manufacturing units 18 and then the manufacturing unit 18 are allowed to stand until the block 181 reaches a predetermined temperature.

Next, after the block 181 reaches the predetermined temperature, the manufacturing unit 18A is pulled out, one of the stoppers 181-8 of the slit valve 181-7 is pulled by using a finger or a holding device, causing the slit valve 181-7 to slide so that the pore 181-9 is made to coincide with the slit-hole 181-10, and the slit valve 181-7 is opened. As has already been stated, the piston 181-3 is alternately pushed in and the precipitant solution is mixed with the bio-polymer solution, after which one of the pistons 181-3 is pushed in in order to collect the mixed solution in the crystallization chamber 181-11. Thereafter, to prevent the piston 181-3 from moving, the slit valve 181-7 is closed by pulling the other stopper 181-8 of the slit valve 181-7.

Next, the manufacturing unit 18A is housed in the housing section 17. Then, the same operation is performed on the other manufacturing unit 18B formed in a pair and on all the other manufacturing units.

Next, the scanning block 214 (see FIG. 10) is moved, and the crystallization chamber 181-11 is observed. When a block 181 which is not worth growing is found, the block 181 is replaced, the slit valve 181-7 is operated and the manufacturing unit 18 is housed by the same operation as described above. Then, the manufacturing unit 18 is allowed to stand as it is for a time necessary for the crystal to grow. When the crystallization chamber 181-11 is observed and it is determined during this period that it is not necessary to continue to grow the crystal, it is possible to replace the manufacturing units 18A and 18B in one partition of the constant-temperature tank 19 in the same way as in the above-described operation. In this way, an unnecessary grow step can be avoided, and the efficiency of manufacturing crystals can be improved.

Next, after the crystal has been grown, the manufacturing unit 18 is pulled out, and the block 181 is replaced in the same manner as in the above-described operation. Thereafter, the next crystal growth is started again. By repeating the above operation, it is possible to grow a great number of bio-polymer crystals by using one apparatus for manufacturing bio-polymer crystals.

In this embodiment, by setting the direction the block 181 is mounted at a position rotated 90° in the plane of the cell mount 182, it is possible to change the direction in which the slit valve 181-7 is pulled out to a back and forth direction of the cell mount to the direction at right angles to the back and forth direction within the plane of the cell mount 182. Since the cell mount is usually formed into a rectangle which is long in the back and forth direction, the slit valve 181-7 is pulled out above and below the cell mount mounted in the apparatus, thereby making the operation easy.

A second embodiment of the present invention is concerned with an improvement in the operation for opening and closing the slit valve 181-7 in the first embodiment.

In this embodiment, referring to FIG. 11, a jack mounting area 182-1 is provided on the cell mount 182 in such a way that the jack mounting area 182-1 is adjacent to the side of the block 181 from which the stopper 181-8 projects. A jack 22 has a rack 222 which is driven by a pinion 223 housed in a box 227 and a press gear 224. The pinion 223 projects on the top surface of the box 227, is moved in linkage with a stem 225 which is bent horizontally and driven by the rotation of a handle 226 disposed in the tip of the stem 225. The rack 222 projects from the opening on the side of the box 227 toward the block 181, which side faces the block 181, and a holding section 221 which is connected to the stopper 181-8 is disposed in the tip of the rack 222. The holding section 221 is shaped like a vertical cylinder having one slit provided therein. When the holding section 22 is inserted into the stopper 181-8, the slit valve 181-7 is loosely inserted into the slit.

In this embodiment, the slit valve 181-7 is opened and closed as follows: first, referring to FIG. 11, the jack 22 having a base 228 removed is fixed in the jack mounting area 182-1 on the cell mount 182 by using, for example, a magnet. At this time, the jack 22 is operated so that the stopper in the upper step is passed through the cylinder of the holding section 221 and the stopper in the lower step is inserted thereto. Then, the handle 226 is rotated to retract the rack 222 and to pull out the stopper 181-8 of the lower step.

Next, the jack 22 is removed, the rack 222 is pulled out, the base 228 at the same height as that of the block 181 in the lower step is fixed to the bottom surface of the box 227, the jack 22 to which the base 228 is fixed is fixed onto the jack mounting area 182-1. At this time, the stopper in the upper step is inserted into the cylinder of the holding section 221. Then, in the same manner as in the lower step, the slit valve 181-7 of the block 181 in the upper step is pulled out. Finally, the jack 22 is removed. Similarly, the slit valve 181-7 is closed by pushing the rack 222.

Referring to FIGS. 12A and 12B, in this embodiment, blocks 181A, 181B are mounted in two adjacent places on the cell mount, and jack mounting areas 182-1A and 182-1B are provided on both sides of the block 181 (the front end portion and the back end portion of the cell mount). The opening and closing of the slit valve is performed in accordance with the following procedures. The jack 22 is fixed to the jack mounting area 182-1A, the slit valve of the block 181A which is adjacent to the jack 22 is closed/opened and then the jack 22 is moved to the jack mounting area 182-1B and the slit valve of the block 181B is closed/opened.

The other construction and the other operations of this embodiment are the same as those of the first embodiment described above. It is also possible to use a jack having a different mechanism in place of the above-described mechanism.

In a modification of this embodiment, one jack mounting area is provided in the central portion of the cell mount, and a block can be disposed on both sides of the cell mount. By reversing the jack by 180° and fixing it, the slit valves of the blocks on both sides are closed/opened. This example is useful to reduce the area necessary for mounting the jack.

A third embodiment of the present invention is concerned with a batch method cell having a construction different from that of the first embodiment.

Referring to FIG. 13, the block of this embodiment comprises two resin blocks 181-1C and 181-1D which are fixed with their end surfaces abutting each other, and a slit valve 181-7A disposed between the the resin blocks.

A bio-polymer solution storage chamber 181-22 in a column shape which is open in the abutting surface is disposed in one of the resin blocks, 181-1D. In the other block 181-1C, a precipitant solution storage chamber 181-21 in a column shape which is open in the abutting surface is disposed in a state in which the position of the opening is made to coincide with the position of the opening of the bio-polymer solution storage chamber 181-22. Also, an injection hole 181-24 for injecting contents is opened in the bottom portion (refers to the blind tube portion on a side opposite to the opening) of the precipitant solution storage chamber 181-21, which injection hole 181-24 is sealed by a screw 181-25 after the contents of the precipitant solution (or bio-polymer solution) are injected.

The precipitant solution storage chamber 181-21 and the bio-polymer solution storage chamber 181-22 are shut off from each other by the slit valve 181-7A disposed between the two resin blocks 181-1C and 181-1D before the crystal is grown.

Figure 14:
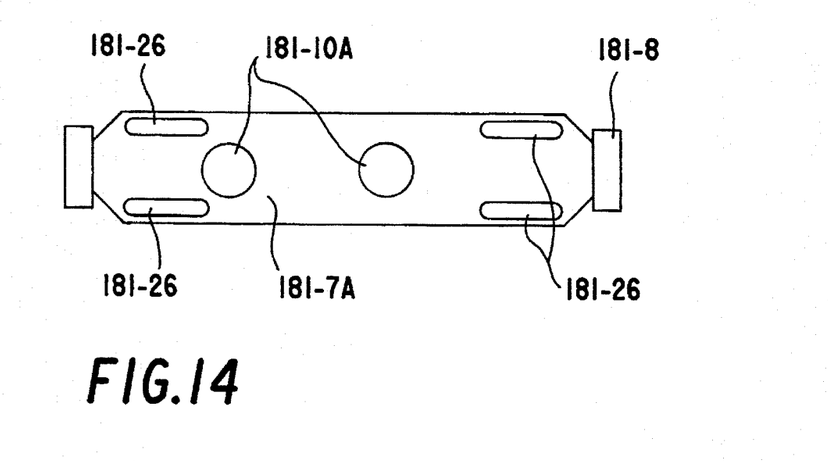
FIG. 14 is a front view illustrating the construction of a slit valve in accordance with the third embodiment of the present invention.

Referring to FIG. 14, the slit valve 181-7A of this embodiment is provided with two openings 181-10A which have the same diameter as that of the bio-polymer solution storage chamber 181-22 in correspondence with the position of the opening of the two bio-polymer solution storage chambers 181-22 disposed in the resin block 181-1D. Escape holes 181-26 in FIG. 14 provided on the right and left, and above and below the slit valve 181-7A are punches with which the set screw 181-6 is loosely engaged when the slit valve 181-7A is made to slide.

In this embodiment, referring to FIGS. 13 and 14, and FIG. 4, first, the manufacturing unit 18 is pulled out, the slit valve 181-7A is pulled so that the opening 181-10A of the slit valve is made to coincide with the opening of the precipitant solution storage chamber 181-21 and the opening of the bio-polymer solution storage chamber 181-22. Next, after the manufacturing unit 18 is housed in the housing section 17, a stirrer 181-23 inside the precipitant solution storage chamber 181-21 is moved and stirred by driving an electromagnet 181-27 secured to the manufacturing unit 18, which electromagnet 181-27 is positioned at end surface on a side opposite to the abutting surface of the resin block 181-1C, and the precipitant is mixed with the bio-polymer solution. After mixing, the stirrer 181-23 is moved to the bottom of the precipitant solution storage chamber 181-21 and made to remain at rest. After this operation, growth of the crystal starts using the precipitant solution storage chamber 181-21 and the bio-polymer solution storage chamber 181-22 as the crystallization chamber 181-11. After the crystal has been grown, the manufacturing unit 18 is pulled out and the slit valve 181-7A is closed to prevent the stirrer 181-23 from moving, after which the block 181 is replaced. This terminates the crystal manufacturing step, and at the same time the next crystal manufacturing step is started. The operation for operating these slit valves, the operation for replacing blocks, and the like are performed in the same way as in the first embodiment described above.

In all the above-described embodiments, needless to say, a block to be replaced is not limited to a particular type. That is, in the case of blocks of different types, referring to FIG. 8, no problem regarding the mounting by replacement and observation occurs when the external shape of the block has a flat shape which engages with the fastener 185, and has the same height and the same side shape so that the block is fastened by the presser 186, and when the observation facility is directly below the observation window 187. However, it is necessary to secure a space as required by which an insertion and pull-out portion can be housed and operated around the block, which portion is caused by operations such as the pull-out of the slit valve, engagement and insertion of the piston 181-3, mounting of the electromagnet 181-27, and the like. The opening and closing of the slit can be performed by push-pulling the slit valve, and pulling out the slit valve in two or three steps.

The present invention can be applied to a vapor diffusion method, a dialysis method, a gradient batch method, and a free-interface diffusion method in place of the above-described batch method.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included within the spirit and scope of the claims. The following claims are to be accorded the broadest interpretation, so as to encompass all such modifications and equivalent structures and functions.

What is claimed is:

1. A manufacturing apparatus to be used in a microgravity environment, when installed in a room of a manned artificial satellite, the apparatus having a top and a bottom, facing each other, and having a front panel disposed between the top and bottom, and secured to the satellite in such a manner that a vertical axis extends through the top and bottom, said apparatus comprising:

(a) a manufacturing unit including a plate or frame-like member having a plane supporting at least a device manipulatable by one hand of an operator, wherein the operator faces the front panel with his head generally opposite the top; and (b) a housing section for housing therein the manufacturing unit, the housing section having means for slidably supporting the manufacturing unit in such a manner that the plane of the plate or frame-like member of the manufacturing unit is generally parallel to the vertical axis and generally perpendicular with the front panel at least when the manufacturing unit is drawn out from the housing section through an opening provided in the front panel.

2. A manufacturing apparatus according to claim 1, wherein a pair of the manufacturing units are housed in the housing section so that the respective planes of the plate or frame-like members of the pair of manufacturing units are in parallel to each other, and wherein the respective at-leastone devices on the planes of the plate or frame-like members of the pair of manufacturing units are arranged symmetrically each other with respect to a virtual plane in parallel to and equidistant from the respective planes of the plate or frame-like members of the pair of manufacturing units.

3. A manufacturing apparatus according to claim 2, further comprising an observation facility for observing the respective devices on the planes of the plate or frame-like members of the pair of manufacturing units, the observation facility being disposed between the respective plate or frame-like members of the pair of manufacturing units.

4. A manufacturing apparatus according to claim 1, further comprising thermal insulation means enclosing the housing section and maintaining the manufacturing units in the housing section at a constant-temperature, wherein a corresponding portion of the thermal insulation means to the opening provided in the front panel is made separable from the apparatus, whereby permitting the manufacturing unit to be drawn out from the apparatus through the thermal insulation means.

5. A manufacturing apparatus according to claim 1, wherein each of the devices comprises a crystallization cell block for growing therein bio-polymer crystals, the crystallization cell block being provided with a window for observing the bio-polymer crystals growing therein.

6. A manufacturing apparatus according to claim 5, wherein the crystallization cell block is removably mounted on the plane of the plate or frame-like member of each manufacturing unit.

7. A manufacturing apparatus according to claim 3, wherein the observation facility comprises a detector and a mechanism for moving the detector to scan the respective planes of the plate or frame-like members of the pair of manufacturing units, whereby a plurality of the devices on the respective planes of the plate or frame-like members of the pair of manufacturing units are observed by the detector.

8. A manufacturing apparatus according to claim 1, wherein the manufacturing apparatus comprises a constant-temperature tank housed therein, the constant-temperature tank being divided into a plurality of chambers by thermal insulation walls, each of the chambers corresponding to the housing section.

9. A manufacturing apparatus to be used in a microgravity environment, when installed in a room of a manned artificial satellite, the apparatus having a top and a bottom, facing each other, and having a front panel disposed between the top and the bottom, and being secured to the satellite in such a manner that a vertical axis extends through the top and bottom, said apparatus comprising:

a constant-temperature tank having therein a plurality of housing sections which are separated from each other by thermal insulation walls, a plurality of manufacturing units each including a cell mount having a plane on which a plurality crystallization cell blocks for growing therein bio-polymer crystals are arranged in line, each of the housing sections housing therein a pair of the manufacturing units, and supporting the manufacturing units in such a manner that the respective planes of the cell mounts face each other and are generally parallel to the vertical axis and generally perpendicular with the front panel and so that the manufacturing units are movable in the direction parallel to the planes of the cell mounts so as to be drawn out from the apparatus through an opening provided in the front panel, and an observation facility disposed between the planes of the cell mounts of the pair of manufacturing units, the observation facility including a detector and a mechanism for moving the detector to scan respective plurality of the crystallization cell blocks on the planes of the cell mounts of the pair of manufacturing units so that the plurality of the crystallization cell blocks are observed by the detector.

* * * * *